(12) United States Patent
Favreau et al.

(10) Patent No.: US 12,109,372 B2
(45) Date of Patent: Oct. 8, 2024

(54) AGENT DELIVERY DEVICES

(71) Applicant: Boston Scientific Scimed, Inc., Maple Grove, MN (US)

(72) Inventors: John Thomas Favreau, Spencer, MA (US); Stan Robert Gilbert, Litchfield, NH (US); Jennifer Mague, Marlborough, MA (US); Andrew Pic, Northboro, MA (US); Matthew LaPlaca, Franklin, MA (US); Jennifer Golden, Norton, MA (US); Jennifer Whelehan, Cortlandt Manor, NY (US); Travis Henchie, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 549 days.

(21) Appl. No.: 17/109,537

(22) Filed: Dec. 2, 2020

(65) Prior Publication Data
US 2021/0162175 A1    Jun. 3, 2021

Related U.S. Application Data

(60) Provisional application No. 62/942,887, filed on Dec. 3, 2019.

(51) Int. Cl.
*A61M 25/01* (2006.01)
*A61M 5/145* (2006.01)
(Continued)

(52) U.S. Cl.
CPC ...... *A61M 25/0136* (2013.01); *A61M 5/1452* (2013.01); *A61M 25/0043* (2013.01);
(Continued)

(58) Field of Classification Search
CPC ............ A61B 17/3478; A61M 5/3294; A61M 5/1452; A61M 5/19; A61M 5/1409;
(Continued)

(56) References Cited

U.S. PATENT DOCUMENTS 5,415,631 A    5/1995  Churinetz
5,674,205 A   10/1997  Pasricha et al.
(Continued)

FOREIGN PATENT DOCUMENTS

EP       2383009 A1    11/2011
KR   101759272 B1 *    7/2017  .......... A61M 5/2448
(Continued)

*Primary Examiner* — Jason E Flick
*Assistant Examiner* — Adam J. Cermak
(74) *Attorney, Agent, or Firm* — Bookoff McAndrews, PLLC (57) ABSTRACT

A medical device may include a handle and a flexible sheath extending from the handle. The sheath may include a first chamber configured to receive a first agent and a second chamber configured to receive a second agent. Each of the first chamber and the second chamber may be disposed in a distal portion of the sheath.
The sheath may also include a first piston received within the first chamber and a second piston received within the second chamber and at least one actuation element configured to transmit a force from the handle to each of the first piston and the second piston. In a first configuration, the first agent may be maintained within the first chamber and the second agent is maintained within the second chamber. In a second configuration, the first agent may be released from the first chamber to mix with the second agent.

19 Claims, 7 Drawing Sheets

(51) Int. Cl.
*A61M 5/32* (2006.01)
*A61M 25/00* (2006.01)
*A61M 25/09* (2006.01)

(52) U.S. Cl.
CPC ........... *A61M 25/09* (2013.01); *A61M 5/3294* (2013.01); *A61M 2025/091* (2013.01); *A61M 2025/09116* (2013.01); *A61M 2205/073* (2013.01)

(58) Field of Classification Search
CPC ............ A61M 5/1407; A61M 25/0074; A61M 25/0075; A61M 2039/222; A61M 31/07; A61M 39/0069
See application file for complete search history.

(56) References Cited

U.S. PATENT DOCUMENTS

| | | | |
|---|---|---|---|
| 5,814,022 A | 9/1998 | Antanavich et al. | |
| 6,004,295 A | 12/1999 | Langer et al. | |
| 6,050,986 A * | 4/2000 | Hektner | A61M 29/02 606/213 |
| 6,659,996 B1 * | 12/2003 | Kaldany | A61M 37/0069 604/509 |
| 7,270,654 B2 * | 9/2007 | Griego | A61M 25/0026 604/82 |
| 8,137,320 B2 * | 3/2012 | Mark | A61B 90/39 604/167.03 |
| 8,357,169 B2 * | 1/2013 | Henniges | A61B 17/8816 606/92 |
| 8,562,642 B2 * | 10/2013 | Oyola | A61B 18/20 606/213 |
| 9,039,761 B2 * | 5/2015 | Trogden | A61F 9/0017 623/6.12 |
| 9,878,106 B2 * | 1/2018 | Naftalovitz | A61M 5/31511 |
| 9,919,111 B2 * | 3/2018 | Hyde | A61M 5/422 |
| 11,020,160 B2 * | 6/2021 | Dewey | A61B 17/8825 |
| 2001/0023346 A1 * | 9/2001 | Loeb | A61M 25/0662 604/508 |
| 2002/0193732 A1 * | 12/2002 | Naimark | A61M 5/142 604/84 |
| 2005/0165354 A1 | 7/2005 | Schwartz et al. | |
| 2010/0174162 A1 * | 7/2010 | Gough | A61M 25/0084 604/82 |
| 2010/0298811 A1 * | 11/2010 | Connair | A61M 5/002 604/82 |
| 2010/0331868 A1 * | 12/2010 | Bardy | A61M 37/0069 606/167 |
| 2011/0146692 A1 * | 6/2011 | Callaghan | A61F 6/225 606/1 |
| 2011/0245866 A1 * | 10/2011 | Cassingham | A61B 17/00491 606/213 |
| 2012/0111336 A1 * | 5/2012 | LaPlaca | A61F 6/22 128/831 |
| 2012/0191101 A1 | 7/2012 | Roth et al. | |
| 2013/0115569 A1 * | 5/2013 | Lambert | A61M 5/31596 433/90 |
| 2015/0025455 A1 * | 1/2015 | Shetty | A61M 5/31515 604/91 |
| 2016/0287809 A1 * | 10/2016 | Sharma | A61M 25/0108 |
| 2016/0325047 A1 * | 11/2016 | Vedrine | A61M 5/31505 |
| 2017/0014569 A1 * | 1/2017 | Flanagan | A61M 5/155 |
| 2017/0095643 A1 * | 4/2017 | Flanagan | A61M 25/0084 |
| 2017/0189649 A1 * | 7/2017 | Anderson | A61D 19/027 |
| 2018/0085555 A1 * | 3/2018 | Flanagan | A61M 25/0662 |
| 2020/0245989 A1 * | 8/2020 | Cawthon | A61B 17/00491 |
| 2020/0289793 A1 * | 9/2020 | Morris | A61N 5/1007 |

FOREIGN PATENT DOCUMENTS

| | | | |
|---|---|---|---|
| WO | 93/02720 A1 | 2/1993 | |
| WO | 2005/048977 A2 | 6/2005 | |
| WO | 2008/103296 A1 | 8/2008 | |
| WO | WO-2013188931 A1 * | 12/2013 | .......... A61M 5/2448 |
| WO | 2014/197685 A1 | 12/2014 | |

* cited by examiner

AGENT DELIVERY DEVICES

CROSS-REFERENCE TO RELATED APPLICATION(S)

This application claims the benefit of priority of U.S. Provisional Patent Application No. 62/942,887, filed Dec. 3, 2019, the entirety of which is incorporated herein by reference.

TECHNICAL FIELD

The present disclosure relates generally to agent delivery devices. More particularly, the present disclosure relates to catheter devices for delivering one or more agents endoscopically.

BACKGROUND

Agents may be delivered during medical procedures, such as endoscopic procedures. During an endoscopic procedure, a user inserts a sheath of an endoscope into a body lumen of a patient. The user utilizes a handle of the endoscope to control the endoscope during the procedure. Tools are passed through a working channel of the endoscope via, e.g., a port in the handle, to deliver treatment at the procedure site, near a distal end of the endoscope. The procedure site is remote from the operator.

During an endoscopic procedure, agents may be delivered by a device inserted into the working channel of the endoscope. If an agent is introduced to the device at its proximal end, the port, some of the agent may be retained within portions of the device within the working channel and may not be delivered to the procedure site. However, a user may desire to deliver an entirety or near an entirety of an agent, without leaving leftover agent in the device. Therefore, a need exists for agent delivery devices.

SUMMARY

Examples of the present disclosure relate to, among other things, agent delivery devices. Each of the examples disclosed herein may include one or more of the features described in connection with the disclosed examples.

In an example, a medical device may comprise a handle and a flexible sheath extending from the handle. The sheath may include a first chamber configured to receive a first agent and a second chamber configured to receive a second agent. Each of the first chamber and the second chamber may be disposed in a distal portion of the sheath. The sheath may also include a first piston received within the first chamber and a second piston received within the second chamber and at least one actuation element configured to transmit a force from the handle to each of the first piston and the second piston. When the handle is in a first configuration, the first agent may be maintained within the first chamber and the second agent is maintained within the second chamber. When the handle is in a second configuration, the first agent may be released from the first chamber to mix with the second agent.

Any of the exemplary medical devices disclosed herein may include any of the following features. The second chamber may be defined by a tube disposed within the first chamber. A wall of the tube may include a plurality of holes. A distalmost end of the tube may be proximal of an opening in a distalmost end of the sheath. A central longitudinal axis of the tube may be approximately coaxial with a central longitudinal axis of the first chamber. The first piston may have an outer perimeter and an inner perimeter. The second piston may have an outer perimeter with a shape that is complementary to a shape of the inner perimeter of the first piston. The first actuation element may be a tube defining a lumen. The second actuation element may be a wire within the lumen. The at least one actuation element may include a first flexible actuation element having a proximal end operatively coupled to the handle and a distal end operatively coupled to the second piston, and a second flexible actuation element having a proximal end operatively coupled to the handle and a distal end operatively coupled to the second piston. The first actuation element may include a wire. The second actuation element may include a wire or a tube. The wire of the first actuation element may be disposed within a lumen of a tube of the second actuation element. The sheath may include at least one barrier preventing a release of the first agent from the first chamber. The at least one actuation element may include a pneumatic fluid. The first chamber may be pre-loaded with the first agent. The second chamber may be pre-loaded with the second agent. The distal portion of the sheath may be removably attached to a remainder of the sheath.

In another example, a medical device may comprise a handle including an actuator; and a sheath extending from the handle. A distal portion of the sheath may include: a first chamber configured to receive a first agent and a tube disposed within the first chamber. The tube may have an internal lumen defining a second chamber. A wall of the tube may include a plurality of holes. The distal portion of the sheath may also include at least one actuation element operatively to transmit a force from the actuator to each of a first piston received within the first chamber and a second piston received within the second chamber. Each of the plurality of holes may be configured to isolate the first agent from the second agent when the at least one actuation element receives no force and to release the second agent from the second chamber through the plurality of holes to mix with the first agent when the at least one actuation element receives the force.

Any of the exemplary medical devices disclosed herein may include any of the following features. The actuation element may include at least one of a wire, a tube, or a fluid. The at least one actuation element may be a first actuation element. The medical device may further comprise a second actuation element. The second actuation element may include at least one of a wire or a tube.

In another example, a medical device may comprise: a handle including an actuator and a sheath extending from the handle. The sheath may include: a first chamber configured to receive a first agent and a second chamber configured to receive a second agent, Each of the first chamber and the second chamber may be disposed in a distal portion of the sheath. The sheath may also include a first piston received within the first chamber and a second piston received within the second chamber; and a tube configured to transmit a force from the actuator to at least one of the first piston and the second piston.

Any of the medical devices disclosed herein may include any of the following features. The second chamber may be defined by a tube disposed within the first chamber. A radial wall of the tube may include a plurality of holes.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator, and the term "proximal" refers to a direction toward an operator. The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate examples of the present disclosure and together with the description, serve to explain the principles of the disclosure.

FIGS. 2A-4B show exemplary distal ends of the agent delivery device of FIG. 1.

DETAILED DESCRIPTION

An agent delivery device may be configured to house an agent at a distal end of the delivery device so that, after the agent is deployed to a treatment site, an amount of agent remaining within the delivery device is minimal and waste of the agent is avoided. The delivery device may be configured to house single component agents or multi-component agents. In the case of multi-component agents, the delivery device may be configured to allow for mixing of the components, prior to delivery from the device. Various mechanisms may be utilized in order to actuate the delivery device to deliver the agent. These mechanisms may include pneumatics, wires, tubes, or any suitable combination thereof.

Figure 1:
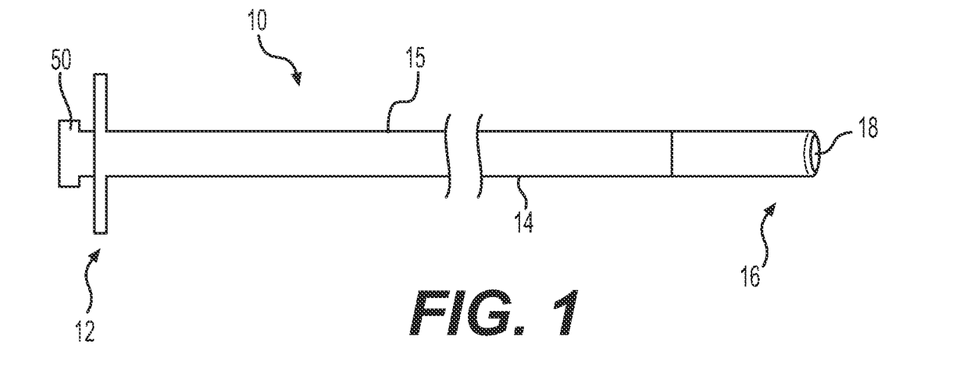
FIG. 1 shows an exemplary agent delivery device.

FIG. 1 depicts an exemplary delivery device 10. Delivery device 10 may include a handle 12 (which may be an operation portion) and a sheath 14 (which may be an insertion portion). Sheath 14 may include a catheter 15 or other suitable component. Sheath 14, or at least components of sheath 14 (such as catheter 15), may be flexible so that sheath 14 may be advanced through a working channel of an endoscope in a body lumen, which may be tortuous. A cross-sectional diameter of sheath 14 may be such that sheath 14 can be advanced through a working channel of an endoscope. A lumen 20 (see FIGS. 2A-4B) may extend from a proximal portion of catheter 15 to a distal end of catheter 15.

Sheath 14 may also include a distal portion 16. Distal portion 16 may be a separate component from catheter 15 or may be a single, unitary structure with catheter 15. Distal portion 16 may be rigid or flexible and may be sized so as to permit advancement of distal portion 16 through a working channel of an endoscope. Distal portion 16 may be fixedly or removably attached to a distal end of catheter 15. Distal portion 16 may be configured to house an agent in, for example, a compartment. Distal portion 16 may have various configurations, as discussed herein with respect to FIGS. 2A-4B.

FIGS. 2A-4B show cross-sectional views of exemplary distal portions 16, 116, 216 of delivery device 10. The features of distal portions 16, 116, 216 may be combined with one another in any suitable combination. Where possible, like reference numbers are used to indicate corresponding structures.

Figure 2A:
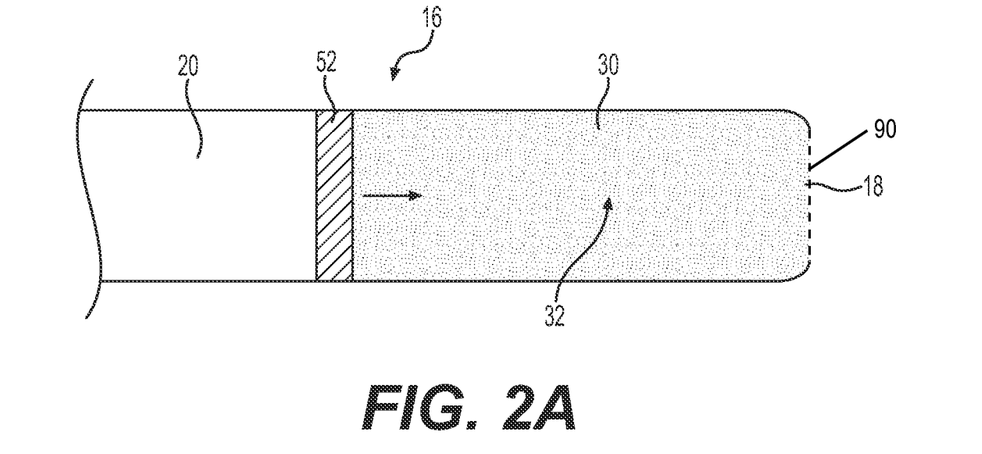
Figure 2B:
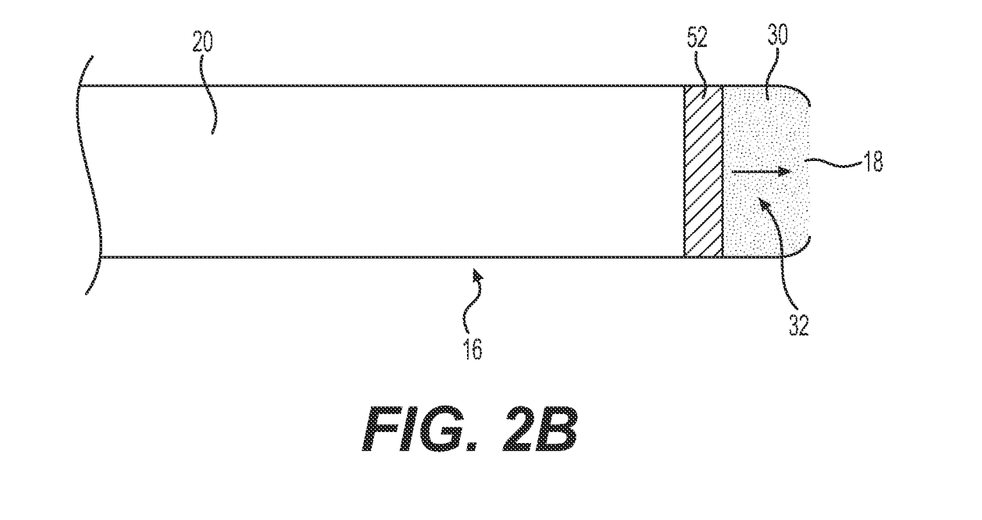

FIGS. 2A and 2B show an example distal portion 16. Distal portion 16 may include a chamber 30 for housing an agent 32. Chamber 30 may be defined by the same surface(s) that define(s) lumen 20. For example, inner surfaces of catheter 15 may define lumen 20 and chamber 30 in configurations where distal portion 16 is a single, unitary structure with catheter 15. Alternatively, chamber 30 may be defined by other surface(s). Although chamber 30 is shown as occupying an entire cross-sectional width of a lumen defined by distal portion 16, chamber 30 may be a subset of distal portion 16. For example, a tube or similar structure may be disposed within distal portion 16, and chamber 30 may be located within the tube or other structure. Opening 18 may be in fluid communication with chamber 30 so that agent 32 may pass through opening 18 when desired by a user, as described below.

A piston 52 may be slidably housed within at least one of chamber 30 and lumen 20. Piston 52 may be fitted with a seal to prevent agent 32 from moving proximally past piston 52. Piston 52 may be configured to move proximally and/or distally within chamber 30. An actuator 50 of handle 12 (FIG. 1) may be used to move piston 52. Actuator 50 may include a plunger, as shown in FIG. 1, or alternative structures, such as those discussed below. For example, actuator 50 may include a knob, a button, a switch, a lever, a slider, or another structure. Exemplary mechanisms for operatively connecting actuator 50 to piston 52 are discussed in further detail with respect to FIGS. 5A-6J, below.

Agent 32 may be any suitable type of agent in any suitable form. Agent 32 may be a gel, liquid, powder, etc. For example, agent 32 may include a hemostatic agent, a clotting agent, a drug or other medicament, etc. Agent 32 may come preloaded in distal portion 16. Where agent 32 is preloaded, delivery device 10 or portions of delivery device 10 may be single-use. Alternatively, a user may load agent 32 into distal portion 16. For example, agent 32 may be loaded into distal portion 16 by withdrawing actuator 50 to move piston 52 proximally. Distal portion 16 may include markings or other indicators of how much of agent 32 has been loaded into or dispensed from distal portion 16. Distal portion 16 may be removably attached to catheter 15 (e.g., via threads, snap-fit, or other mechanisms) such that a distal portion 16 preloaded with agent 32 in compartment 30 may be attached to a re-usable (or disposable) catheter 15 prior to use. After agent 32 has been dispensed from opening 18, as described below, distal portion 16 may be replaced with a new, preloaded distal portion 16.

Agent 32 may be retained within chamber 30 by various mechanisms. For example, a force of air pressure on agent 32 may retain agent 32 within chamber 30. A force of gravity may not overcome the air pressure on agent 32, causing agent 32 to be retained within chamber 30. Alternatively, or additionally, a removable barrier 90 may be disposed at or near opening 18. Barrier 90 may be punctured or otherwise removed when, as discussed below, agent 32 is advanced out of opening 18. Additionally or alternatively, a viscosity of agent 32 may be sufficiently high that agent 32 does not pass through opening 18 until actuator 50 is manipulated, as described below.

In FIG. 2A, distal portion 16 is shown in a first configuration. For example, the configuration of FIG. 2A may be a configuration of distal portion 16 prior to administering any of agent 32 to a site of a procedure. Agent 32 may be housed in chamber 30, distal to piston 52. In FIG. 2B, distal portion 16 is shown in a second configuration, in which piston 52 has been moved distally of the position shown in FIG. 2A. In the second configuration, at least some of agent 32 may have been administered at a desired site, by the mechanisms described below. In order to transition piston 52 from the first configuration to the second configuration, actuator 50 may be manipulated. For example, a plunger may be depressed or another mechanism may be activated to cause piston 52 to move distally, as described in further detail below (see FIGS. 5A-6J). As piston 52 moves distally toward opening 18, piston 52 may push agent 32 out of opening 18. Piston 52 and/or chamber 30 may be configured so that all or approximately all of agent 32 may be delivered to a procedure site or to another chamber via opening 18 when piston 52 is fully distally advanced. Only an amount of agent 32 that is desired to be delivered to a procedure site may be loaded into chamber 30 so as to avoid waste of agent 32. As agent 32 is pushed out of opening 18, the force of agent 32 (transmitted from piston 52) may break or otherwise puncture any barrier 90 over opening 18.

Figure 3A:
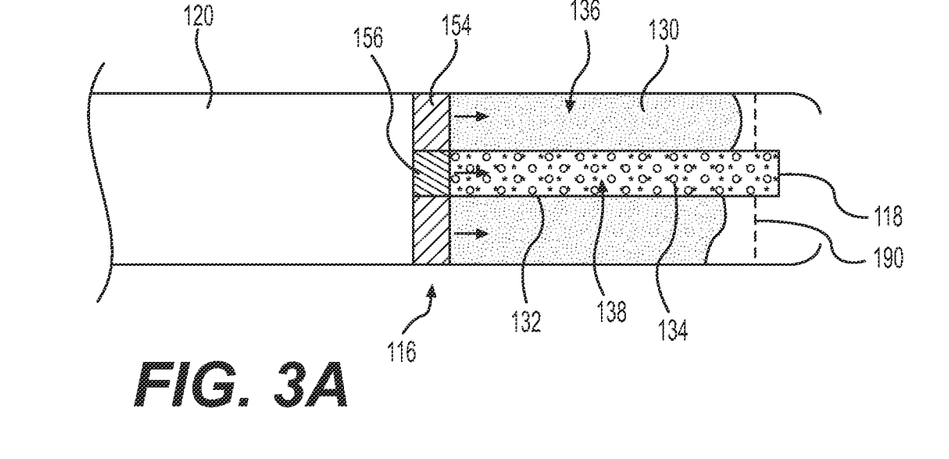
Figure 3B:
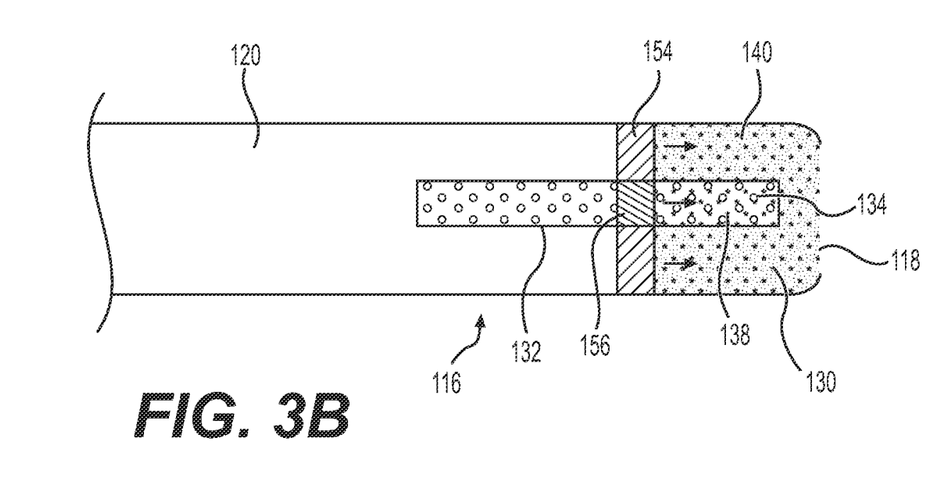

FIGS. 3A and 3B show an alternative distal portion 116, which may have any of the properties of distal portion 16 and which may be used in conjunction with as part of delivery device 10. Distal portion 116 may facilitate mixing of multi-component agents and delivery of a mixed agent to a procedure site. Distal portion 116 may include a chamber 130, which may have any of the properties of chamber 30. A tube 132 may be housed within chamber 130. Tube 132 may have an internal lumen that defines a chamber for receiving an agent, as described below. Tube 132 and chamber 130 may be coaxial/concentric or may have parallel longitudinal axes. Alternatively, longitudinal axes of tube 132 and 130 may be transverse to one another. Tube 132 may have a round cross-sectional shape or an alternative shape (e.g., square, rectangular, polygonal, oval, etc.). Tube 132 may be fenestrated such that at least a radially outer wall of tube 132 includes a plurality of holes 134. Holes 134 may have any suitable shape (e.g., a round shape). Further details of holes 134 are provided below. Tube 132 may also optionally include a distal opening (not shown), or a distally-facing wall with or without holes 134. A first component agent 136 may be housed within chamber 130, and a second component agent 138 may be housed within a lumen of tube 132.

A first piston 154 may be slidably disposed within chamber 130 (or lumen 120). First piston 154 may have a washer shape, with a central opening, so that tube 132 fits within the central opening. First piston 154 may movably slide around an outer surface of tube 132. A second piston 156 may be disposed within the central opening of, and slidably disposed within, tube 132. Second piston 156 may have a shape and size that mates with a central opening of first piston 154. First piston 154 may form a seal with outer walls of tube 132 and inner walls of chamber 130 to prevent passage of first component agent 136 proximally past first piston 154. Second piston 156 may form a seal with inner walls of tube 132 such that second component agent 138 may not move distally past second piston 156. An outer perimeter of first piston 154 may have a complementary shape to walls of tube 132, and an inner perimeter of first piston 154 may have a complementary shape to an outer surface of tube 132 and an outer perimeter of second piston 156.

In a first configuration, as shown in FIG. 3A, tube 132 (including holes 134) and pistons 154, 156 may be configured such that first component agent 136 may be retained within chamber 130 (and external to tube 132) and second component agent 138 may be retained within tube 132. For example, a force of air pressure on component agents 136, 138 may retain component agents 136, 138 within component 130 and tube 132, respectively. Air pressure may retain component agents 136, 138 because such air pressure may have a force that exceeds that of gravity. Holes 134 may be sized such that surface tension of agent 138 or other forces retain second component agent 138 within tube 132 without undesired leaking through holes 134. For example, holes 134 may have a sufficiently small diameter and have a sufficient length through a wall of tube 132 such that component agents 136, 138 do not pass through holes 134 until a force is exerted by piston 156. Additionally or alternatively, a viscosity of component agents 136, 138 may be such that they do not pass through holes 134 until a force is exerted by piston 156. Holes 134 may also be covered by a movable/removable barrier, which may have any of the features of barrier 90. Chamber 130 may also include a barrier 190 at or proximal to opening 118, which may have any of the features of barrier 90. Holes 134 may be approximately 0.1 microns to 2 millimeters in width (e.g., diameter). Holes 134 may be uniform or may vary (e.g., different sizes and/or shapes of holes 134 may deliver second component agent 138 at varying rates). Holes 134 may be circular or may have an alternative shape (e.g., oval, polygon, slit, etc.). As described above with respect to distal portion 16, distal portion 116 may be pre-loaded with component agents 136, 138. Alternatively, a user may load component agents 136, 138 within chamber 130 and tube 132, respectively.

FIG. 3B shows a second configuration of distal portion 116, in which pistons 154, 156 have been advanced distally through chamber 130 and tube 132, respectively. Pistons 154, 156 may be configured to move together or independently to facilitate intended mixing of first component agent 136 and second component agent 138. As piston 156 is advanced distally through tube 152, second component agent 138 may pass through holes 134 into chamber 130. First component agent 136 may also move distally within tube 152 as a result of distal movement of piston 154. First component agent 136 and second component agent 138 may mix together to form a combined agent 140 within chamber 130. Mixing may be facilitated by presence of an empty portion of chamber 130 that is distal to a distal end of tube 132. For example, a distal end of tube 132 may be proximal to opening 118. Alternatively, mixing may occur in a portion of chamber 130 that includes tube 132 passing therethrough (e.g., in a portion of chamber 130 that is empty of first component agent 136 prior to activation of an actuator. For example, mixing may occur in an area of chamber 130 distal to barrier 190. Distal movement of piston 154 and/or piston 156 may cause combined agent 140 to pass through distal opening 118 and to be delivered to a procedure site. As with distal portion 16 of FIGS. 2A-2B, distal portion 116 may facilitate dispensing of all or substantially all of first component agent 136 and second component agent 138, combined into combined agent 140. Thus, distal portion 116 may avoid waste of first component agent 136 and second component agent 138.

Although FIGS. 3A and 3B show one tube 132 and one chamber 130, it will be appreciated that more than one tube 132 or chamber 130 may be used (for example, should a mixture of three or more components be desired). An appropriate number of corresponding pistons (e.g., pistons 152, 154) may be used.

Figure 4A:
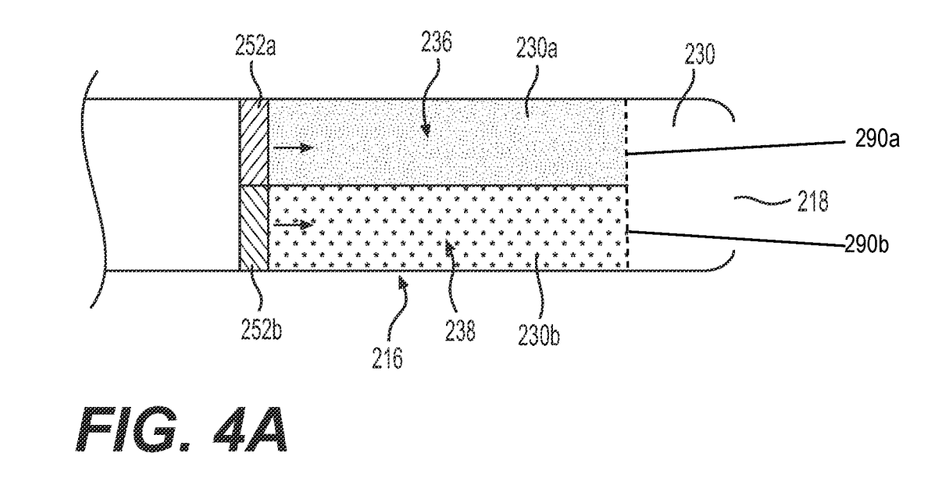
Figure 4B:
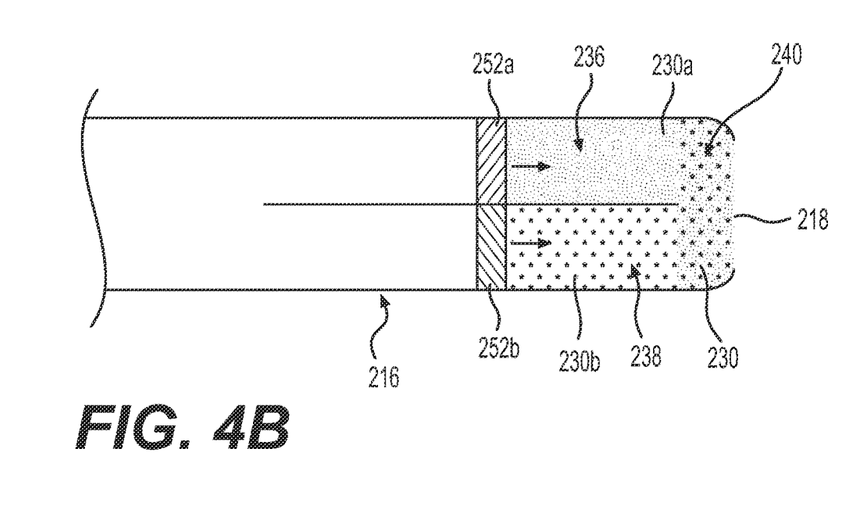

FIGS. 4A and 4B show another alternative distal portion 216, which may have any of the properties of distal portions 16, 116, described above. Distal portion 216 may include a chamber 230 having multiple sub-chambers 230a, 230b.

Sub-chambers 230a, 230b may be defined by tubes contained within chamber 230. Alternatively, sub-chambers 230a, 230b may be formed by a divider extending longitudinally between sub-chambers 230a, 230b, so that sub-chambers 230a, 230b are defined by inner walls of chamber 230 and by the divider. While FIGS. 4A and 4B show two sub-chambers 230a, 230b, it will be appreciated that any number of suitable sub-chambers 230a, 230b may be used. Sub-chambers 230a, 230b may be parallel to one another or may be transverse to one another. Each of sub-chambers 230a, 230b may include an opening at its distal end. A first component agent 236 may be housed in a first sub-chamber 230a, and a second component agent 238 may be housed in a second sub-chamber 230b. As shown in FIGS. 4A and 4B, sub-chambers 230a and 230b may be approximately the same size, or sub-chambers 230a and 230b may be different sized. For example, where more of first component agent 236 than second component agent 238 is desired to be used, sub-chamber 230a may be larger than chamber 230b. Sub-chambers 230a, 230b may have uniform cross-sections or may have variable cross-sections designed to effect a desired mixing ratio of first component agent 236 and second component agent 238.

A first piston 252a may be slidably disposed within first sub-chamber 230a. A second piston 252b may be slidably disposed within second sub-chamber 230b. First piston 252a may form a seal with inner surface(s) of first sub-chamber 230a, and second piston 252b may form a seal with inner surface(s) of second sub-chamber 230b. First piston 252a may be jointly or independently movable with second piston 252b. As first piston 252a and/or second piston 252b are advanced distally, first component agent 236 and/or second component agent 238, respectively, may be advanced distally. First component agent 236 and second component agent 238 may mix to form a combined agent 240 in a portion of chamber 230 that is distal to distal openings of sub-chambers 230a, 230b. Combined agent 240 may be pushed out of distal opening 218 as pistons 252a, 252b advance distally. As with distal portions 16, 116 of FIGS. 2A-3B, distal portion 216 may facilitate dispensing of all or substantially all of first component agent 236 and second component agent 238, combined into combined agent 240. Thus, distal portion 216 may avoid waste of first component agent 236 and second component agent 238.

Prior to advancing pistons 252a, 252b, first component agent 236 and second component agent 238 may be retained within sub-chambers 230a, 230b, respectively, due to forces of air pressure or a viscosity of component agents 236, 238, as discussed above with respect to FIGS. 2A-3B. Additionally or alternatively, membranes 290a, 290b may be disposed at or near distal ends of sub-chambers 230a, 230b. Membrane 290 may have any of the properties of membrane 90. A membrane (not shown) may also be disposed at or near opening 218 and may have any of the features of membrane 90.

Although FIGS. 4A and 4B show two sub-chambers 230a, 230b, it will be appreciated that any number of sub-chambers may be used, along with an appropriate number of corresponding pistons.

FIGS. 5A-6J show exemplary mechanisms for actuating the pistons of the distal portions pictured in FIGS. 2A-4B. Alternatively, features of FIGS. 5A-6J may be used independently of the distal portions of FIGS. 2A-4B. Similarly, the distal portions of FIGS. 2A-4B may be used with mechanisms other than those described below with respect to FIGS. 5A-6J. Although certain of the actuation mechanisms below may be described as having suitability for certain of the distal portions described above, it will be appreciated that these compatibilities are not limiting and that various combinations of aspects of distal portions and actuation mechanisms may be used. When possible, corresponding reference numbers are used to denote corresponding structures.

Figure 5A:
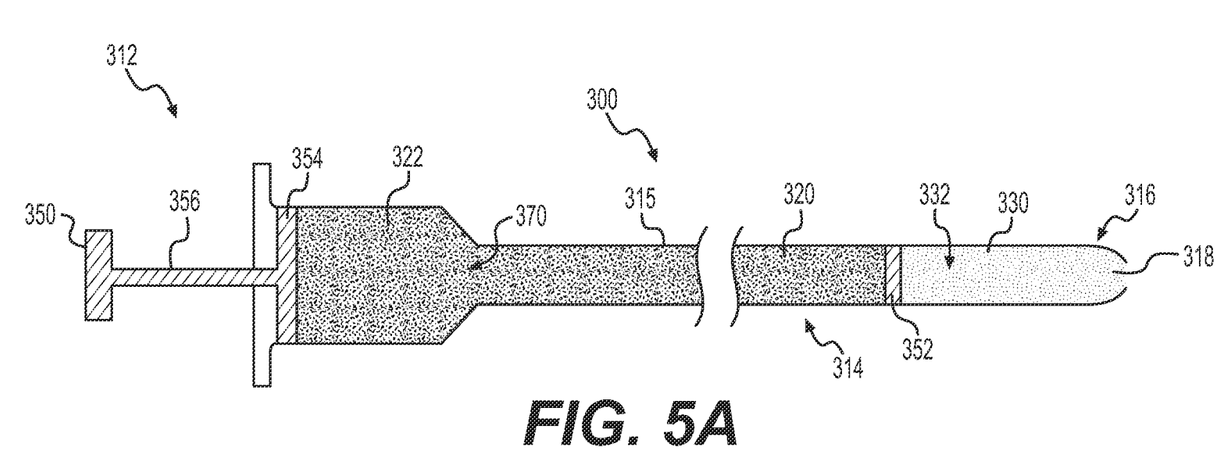
FIGS. 5A-5B show another exemplary agent delivery device.
Figure 5B:
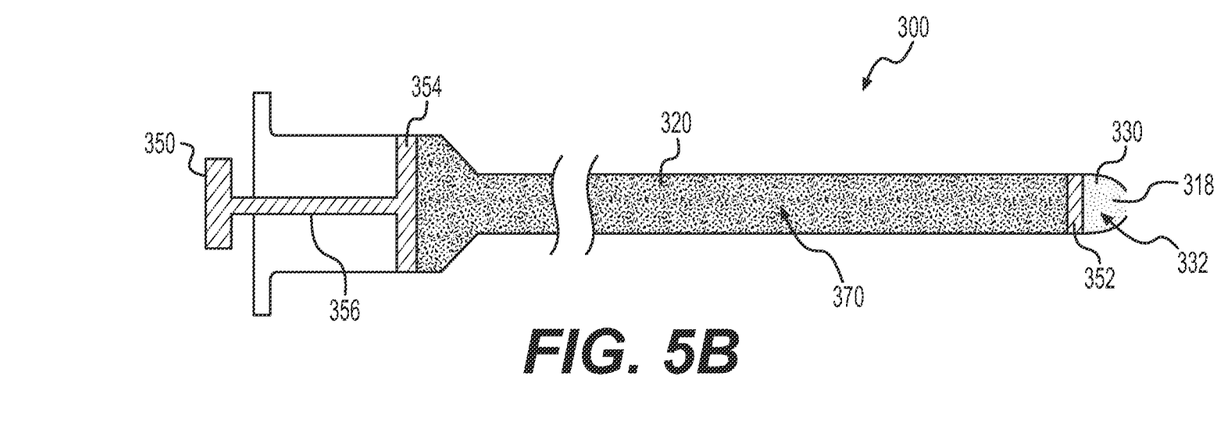

FIGS. 5A and 5B show a cross-section of an example delivery device 300, which may have any of the features of delivery device 10. Delivery device 300 may have a handle 312 (e.g., an operation portion) and a sheath 314 (e.g., an insertion portion). Sheath 314 may include a catheter 315 or other suitable component. A lumen 320 may extend from a proximal portion of catheter 315 to a distal end of catheter 315.

Sheath 314 may also include a distal portion 316. Distal portion 316 may be a separate component from catheter 315 or may be a single, unitary structure with catheter 315. Distal portion 316 may be fixedly or removably attached to a distal end of catheter 315. Distal portion 316 may be configured to house an agent 332. Distal portion 316 may have any of the properties of distal portions 16, 116, 216, described above. Although distal portion 316 is shown as having one chamber 330, it will be appreciated that multiple chambers may be utilized, as shown, for example, in FIGS. 3A-4B. Chamber 330 may terminate in a distal opening 318. An agent 332 may be contained in chamber 330. A piston 352 may be slidable within chamber 330 and may have any of the properties of any of the pistons described above, with respect to FIGS. 2A-4B.

The example of FIGS. 5A-5B may utilize pneumatic actuation mechanisms for causing piston 352 to slidably move within chamber 330. It will be appreciated that the actuation mechanisms of FIGS. 5A-5B may be used in combination with the actuation mechanisms of FIGS. 6A-6J, discussed below. The actuation mechanisms of FIGS. 5A-5B may also be used with device 10, including any of distal ends 16, 116, 216.

Handle 312 may include a plunger 350. Plunger 350 may be operatively connected to a piston 354 via a stem 356. Although piston 354 is described as being disposed within handle 312, it will be appreciated that piston 354 may also be disposed within sheath 314. Handle 312 may include a lumen 322 in which piston 354 is slidably disposed. Piston 354 may form a seal with surfaces of lumen 322. Lumen 322 may have a larger cross-sectional diameter than lumen 320, as shown in FIG. 5A. Alternatively, lumen 322 may have the same cross-sectional diameter to lumen 320 or a smaller cross-sectional diameter than lumen 320. A larger cross-section of lumen 322 may enable device 300 to have a shorter stem 356.

A fluid 370 may be disposed within lumen 322, distal to piston 354 and proximal of piston 352. Pistons 352, 354 may include sealing features that retain fluid 370 between piston 352 and piston 354. FIG. 5A shows delivery device 300 in a first configuration, in which plunger 350 has not been depressed and agent 332 has not been dispensed via opening 318. FIG. 5B shows delivery device 300 in a second configuration, in which plunger 350 has been at least partially depressed so that at least some of agent 332 has been dispensed via opening 318. As plunger 350 is depressed/advanced distally, piston 354 may advance by a corresponding (e.g., an equivalent) amount. Plunger 350 may exert a force on fluid 370 to advance fluid 370 distally. Fluid 370 may exert a force on piston 352, which, in turn, advances agent 332 through opening 318, as described above, with respect to FIGS. 1-4B.

Fluid 370 may be incompressible or may be compressible. For example, if fluid 370 is incompressible, as plunger 350 is depressed, agent 332 may immediately or approximately immediately be dispensed from opening 318. If fluid 370 is compressible, there may be a delay between depression of plunger 350 and dispensing of agent 332 from opening 318, as fluid 370 is compressed. Fluid 370 may include any suitable fluid. For example, fluid 370 may be bio-compatible and may include saline.

The use of fluid 370 as an actuation mechanism may allow sheath 314 to be flexible such that sheath 314 may be passed through a working channel of an endoscope and through torturous body lumens of a subject. This flexibility of sheath 314 facilitates positioning of agent 332 in distal portion 316, so that agent 332 is not wasted.

Figure 6A:
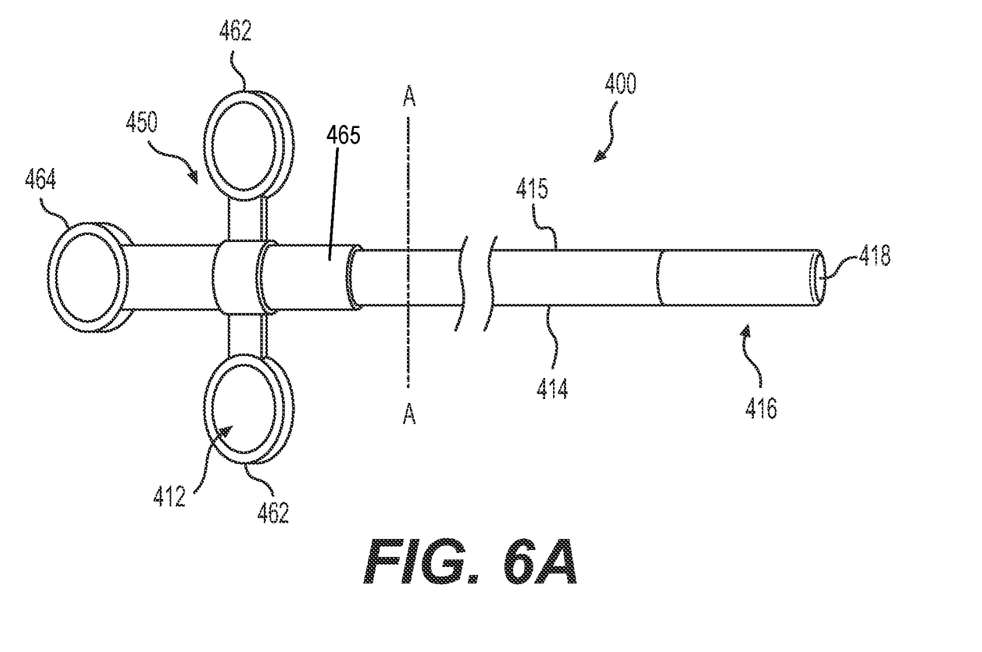
FIGS. 6A-6J show other exemplary agent delivery devices.

FIGS. 6A-6J show alternative actuation mechanisms. FIG. 6A shows a delivery device 400, which may have any of the properties of delivery devices 10, 300. Delivery device 400 may have a handle 412 (e.g., an operation portion) and a sheath 414 (e.g., an insertion portion). Sheath 414 may include a catheter 415 or other suitable component. A lumen 420 may extend from a proximal portion of catheter 415 to a distal end of catheter 415 (see, e.g., FIGS. 6A-6B). Sheath 414 may also include a distal portion 416. Distal portion 416 may be a separate component from catheter 415 or may be a single, unitary structure with catheter 415. Distal portion 416 may be fixedly or removably attached to a distal end of catheter 415. Distal portion 416 may be configured to house an agent. Distal portion 416 may have any of the properties of distal portions 16, 116, 216, 316, described above. FIGS. 6C, 6E, 6F, 6H, and 6J below show exemplary distal portions 464, 466, 468, 470, 472, that may be used in place of distal portion 416. Features of distal portions 464, 466, 468, 470, 472 may be used in combination with any features of distal portions 16, 116, 216, 316, and corresponding structures are identified with like reference numbers.

Handle 412 may include a plunger 450, which may be operatively connected to finger loops 462. Plunger 450 may have a component that is within lumen 420. Handle 412 may also include a proximal thumb loop 464. Advancing finger loops 462 distally over a body 465 of handle 412 may cause plunger 450 to be advanced distally. The features of handle 412 may also be used with handles 12, 312, described above. Plunger 450 may be operatively connected (e.g., mechanically coupled) to the actuation mechanisms described herein, with respect to FIGS. 6B-6J. Features of handle 464, including finger loops 462 and thumb loop 464, also may be used with devices 10, 300, described above.

Figure 6B:
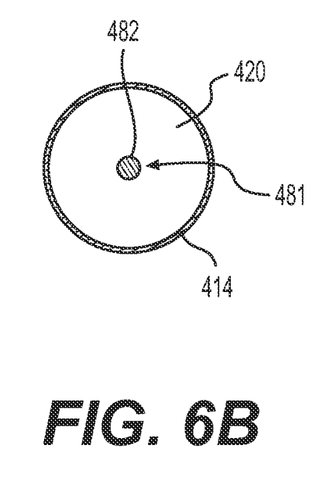
Figure 6C:
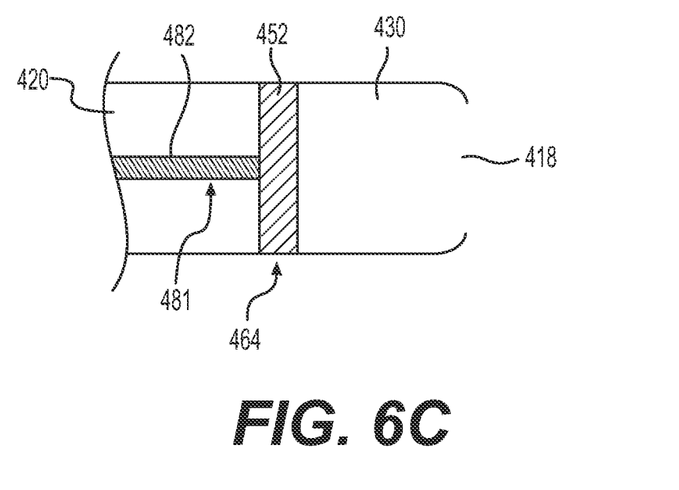

FIG. 6B shows a first exemplary actuation mechanism 481 in cross-section along line A-A, shown in FIG. 6A, and FIG. 6C shows an exemplary cross-section of distal portion 464 that may be used in conjunction with the actuation mechanism of FIG. 6B. As shown in FIG. 6B, an actuation mechanism may include a wire 482, which may be located within lumen 420 of sheath 414. A proximal portion of wire 482 may be operatively coupled to plunger 450 via, e.g., crimping, soldering, gluing, or other fixing mechanisms. Wire 482 and plunger 450 may alternatively be formed of a single, unitary material. A distal portion of wire 482 may be operatively connected (e.g., mechanically connected) to a piston 452, which may slidably movable within a chamber 430. Wire 482 may be crimped, soldered, glued, or otherwise fixed to piston 452. Alternatively, wire 482 and piston 452 may be formed of a single, unitary material. Wire 482 may be made from a flexible material, such as nitinol, stainless steel, flexible plastic, polymer, a braided coil, Nylon-12, or any other suitable material. Wire 482 may be sufficiently rigid so as to transmit a force from movement of plunger 450 to piston 452. However, wire 482 may be sufficiently flexible so as to not inhibit or may not substantially inhibit a flexibility of sheath 414. Although the term "wire" is used, it will be appreciated that wire 482 may encompass structures made of materials such as plastic.

When plunger 450 is advanced distally, wire 482 may transmit the force and/or motion to piston 452, which causes piston 452 to advance, and which may result in dispensing of an agent, as described above, (e.g., with respect to FIGS. 2A-2B).

Figure 6D:
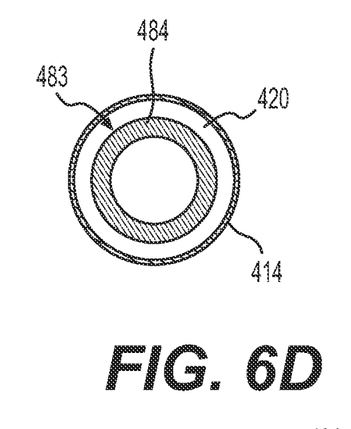
Figure 6E:
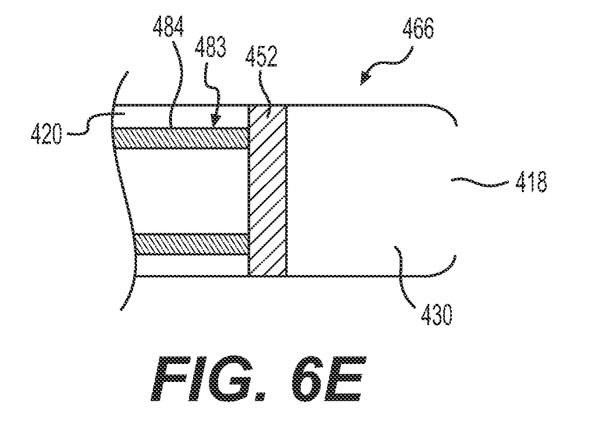
Figure 6F:
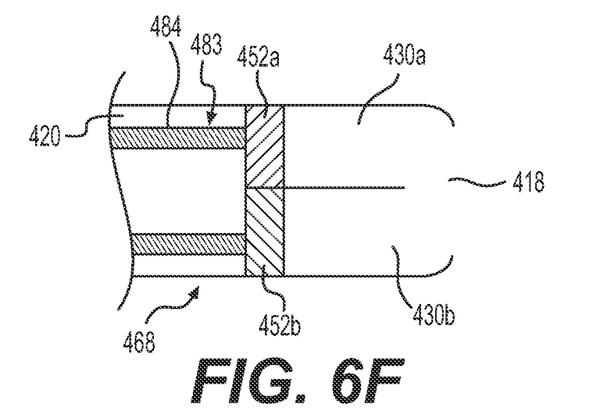

FIG. 6D shows another exemplary actuation mechanism 483 in cross-section along line A-A, shown in FIG. 6A. FIGS. 6E and 6F show exemplary distal portions 466, 468, which may be used in conjunction with the actuation mechanism of FIG. 6D. As shown in FIG. 6D an actuation mechanism may include a tube 484, which may be located within a lumen 420 of sheath 414. A proximal portion of tube 484 may be operatively coupled to plunger 450 via, e.g., crimping, soldering, gluing, or other fixing mechanisms. Tube 484 and plunger 450 may alternatively be formed of a single, unitary material. Tube 484 may have a central lumen or opening extending longitudinally therethrough.

As shown in FIG. 6E, actuation mechanism 483 may be used in conjunction with a distal portion 466 that is similar to distal portion 16 of FIGS. 2A-2B and may have any of the properties of distal portion 16. Distal portion 466 may include one chamber 430, and a piston 452 may be slidably disposed within chamber 430. A distal portion of tube 484 may be operatively connected (e.g., mechanically connected) to piston 452. Tube 484 may be crimped, soldered, glued, or otherwise fixed to piston 452. Alternatively, tube 484 and piston 452 may be formed of a single, unitary material. Tube 484 may be made from a flexible material, such as a plastic material, nitinol, flexible polymer, braided coil, or other suitable material. Tube 484 may be sufficiently rigid so as to transmit a force from movement of plunger 450 to piston 452. However, tube 484 may be sufficiently flexible to not inhibit or may not substantially inhibit a flexibility of sheath 414. Although tube 484 is shown as having a hollow center core, it will be appreciated that tube 484 may also have a solid cross-section, a latticed cross-section, etc.

When plunger 450 is advanced distally, tube 484 may transmit the force from plunger 450 to piston 452, which causes piston 452 to advance, and which may result in dispensing of an agent, as described above (e.g., with respect to FIGS. 2A-2B).

As shown in FIG. 6F, actuation mechanism may 483 may alternatively be used in conjunction with a distal portion 468, which may be similar to distal portion 216 of FIGS. 4A-4B and may have any of the features thereof. Distal portion 468 may include a first chamber 430a and a second chamber 430b. A first piston 452a may be slidably disposed within first chamber 430a, and a second piston 452b may be slidably disposed within second chamber 430b. A distal portion of tube 484 may be operatively connected (e.g., mechanically connected) to first piston 452a and second piston 452b. Tube 484 may be crimped, soldered, glued, or otherwise fixed to first piston 452a and second piston 452b. Alternatively, tube 484 and pistons 452a, 452b may be formed of a single, unitary material. Tube 482 may include slots or other features (not shown) to accommodate wall(s) of first chamber 430a and second chamber 430b between first chamber 430a and second chamber 430b.

When plunger 450 is advanced distally, tube 484 may transmit the force from plunger 450 to both of pistons 452a, 452b, which causes pistons 452a, 452b to advance, which may result in dispensing of an agent, as described above (e.g., with respect to FIGS. 4A-4B).

Figure 6G:
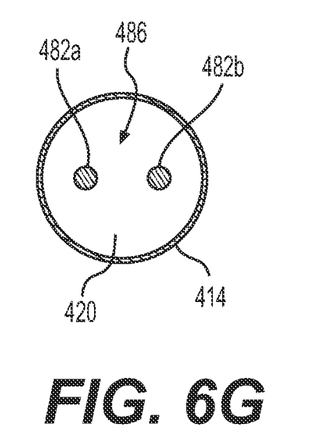
Figure 6H:
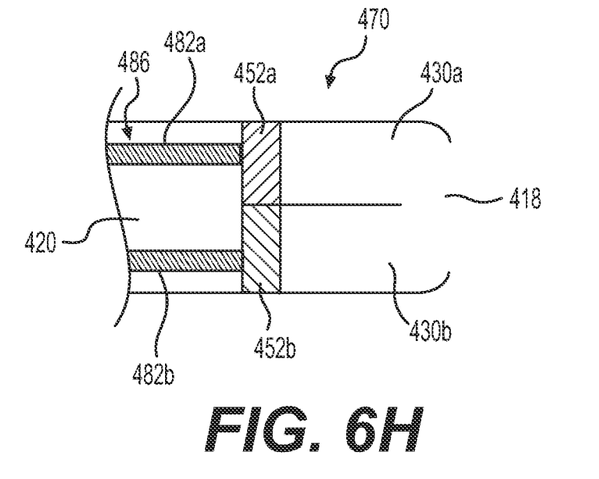

FIG. 6G shows another exemplary actuation mechanism 486 in cross-section along line A-A, shown in FIG. 6A. FIG. 6H shows an exemplary cross-section of distal portion 470 that may be used in conjunction with the actuation mechanism of FIG. 6G. Distal portion 470 may include a first chamber 430a and a second chamber 430b. A first piston 452a may be slidably disposed within first chamber 430a, and a second piston 452b may be slidably disposed within second chamber 430b.

As shown in FIG. 6G, actuation mechanism 486 may include wires 482a and 482b, which may be located within a lumen 420 of sheath 414. Although FIG. 6G shows two wires 482a and 482b, any suitable number of wires may be used. A proximal portion of each of wires 482a, 482b may be operatively coupled to plunger 450 via, e.g., crimping, soldering, gluing, or other fixing mechanisms. Wires 482a, 482b and plunger 450 may alternatively be formed of a single, unitary material. Alternatively, wires 482a and 482b may be independently movable via, for example, multiple plungers (not shown).

A distal portion of wire 482a may be operatively connected (e.g., mechanically connected) to first piston 452a. Wire 482a may be crimped, soldered, glued, or otherwise fixed to first piston 452a. Alternatively, wire 482a and first piston 452a may be formed of a single, unitary material. A distal portion of wire 482b may be operatively connected (e.g., mechanically connected) to second piston 452b. Wire 482b may be crimped, soldered, glued, or otherwise fixed to second piston 452b. Alternatively, wire 482b and second piston 452b may be formed of a single, unitary material.

Wires 482a, 482b may have any of the properties of wire 482, described above. When plunger 450 is advanced distally, wire 482a may transmit the force and/or motion to first piston 452a, which causes piston 452a to advance. Simultaneously (unless wires 482a and 482b are separately controlled), wire 482b may transmit the force and/or motion of plunger 450 to second piston 452b. Advancing plunger 450 distally may result in in dispensing of an agent, as described above (e.g., with respect to FIGS. 4A-4B).

Figure 6I:
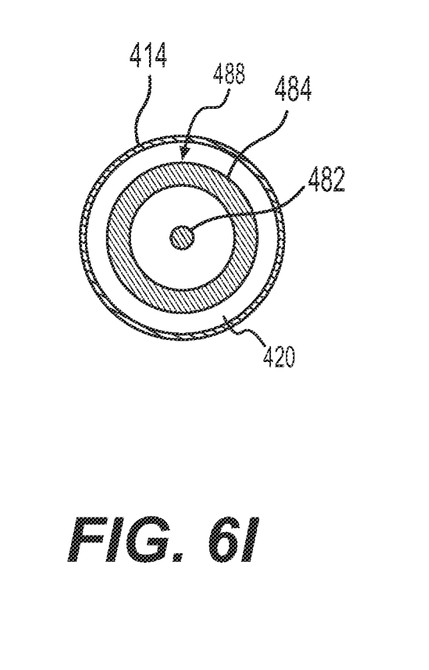
Figure 6J:
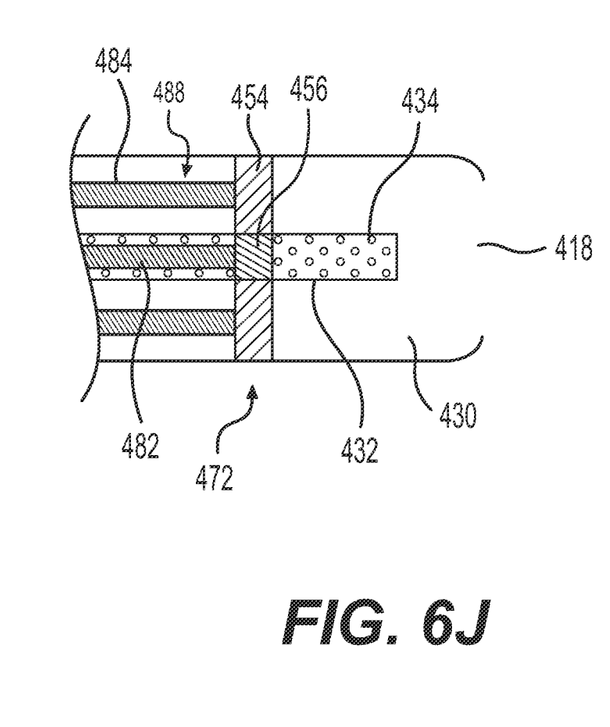

FIG. 6I shows another exemplary actuation mechanism 488 in cross-section along line A-A, shown in FIG. 6A, and FIG. 6J shows an exemplary cross-section of distal portion 472 that may be used in conjunction with actuation mechanism 488. Distal portion 472 may have any of the properties of distal portion 116, described above with respect to FIGS. 3A-3B. Distal portion 472 may include a chamber 430 and a tube 432. A first piston 454 may be slidably disposed within chamber 430, and a second piston 456 may be slidably disposed within tube 432. Tube 432 may include a plurality of holes 434. As shown in FIG. 6J, chamber 430 may include a distally facing opening 418.

As shown in FIG. 6I, actuation mechanism 488 may include wire 482, which may be located within lumen 420 of sheath 414, and may have any of the properties described above with respect to FIG. 6B. A proximal portion of wire 482 may be operatively coupled to plunger 450 via, e.g., crimping, soldering, gluing, or other fixing mechanisms. Wire 482 and plunger 450 may alternatively be formed of a single, unitary material. Actuation mechanism 488 may also include a tube 484, which may also be located within lumen 420 of sheath 414, and which may have any of the properties described above with respect to FIGS. 6D-6F. A proximal portion of tube 484 may be operatively coupled to plunger 450 via, e.g., crimping, soldering, gluing, or other fixing mechanisms. Tube 484 and plunger 450 may alternatively be formed of a single, unitary material. Alternatively, wire 482 and tube 484 may be separately movable. Wire 482 may be located within a tube 484. For example, wire 482 may be coaxial with a central longitudinal axis of tube 484, or may be parallel to the central longitudinal axis of tube 484.

A distal portion of wire 482 may be operatively connected (e.g., mechanically connected) to first piston 456. Wire 482 may be crimped, soldered, glued, or otherwise fixed to first piston 456. Alternatively, wire 482 and first piston 456 may be formed of a single, unitary material. A distal portion of tube 484 may be operatively connected (e.g., mechanically connected) to second piston 454. Tube 484 may be crimped, soldered, glued, or otherwise fixed to second piston 454. Alternatively, tube 484 and piston 454 may be formed of a single, unitary material.

When plunger 450 is advanced, wire 482 may transmit the force from plunger 450 to piston 456, and tube 484 may transmit the force from plunger 450 to piston 454. Advancing plunger 450 distally may result in in dispensing of an agent, as described above (e.g., with respect to FIGS. 3A-3B).

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device comprising:
a handle;
a flexible sheath extending from the handle, wherein the sheath includes:
a first chamber including a first agent and a second chamber including a second agent, wherein each of the first chamber and the second chamber is disposed in a distal portion of the sheath, wherein the first chamber surrounds the second chamber and includes a distally facing opening positioned distal to the second chamber, wherein the second chamber is defined by a first tube disposed within the first chamber, wherein a wall of the first tube includes a plurality of holes;
a first piston received within the first chamber and a second piston received within the second chamber; and
at least one actuation element configured to transmit a force from the handle to each of the first piston and the second piston;
wherein, when the handle is in a first configuration, the first agent is maintained within the first chamber and the second agent is maintained within the second chamber, and wherein, when the handle is in a second configuration, the second agent is released from the second chamber to enter the first chamber and mix with the first agent.

2. The medical device of claim 1, wherein a distalmost end of the first tube is proximal of the distally facing opening of the first chamber.

3. The medical device of claim 1, wherein a central longitudinal axis of the first tube is approximately coaxial with a central longitudinal axis of the first chamber.

4. The medical device of claim 1, wherein the first piston has an outer perimeter and an inner perimeter, and wherein the second piston has an outer perimeter with a shape that is complementary to a shape of an inner wall of the first tube.

5. The medical device of claim 4, wherein the at least one actuation element includes a first actuation element that is a second tube defining a lumen, and wherein the at least one actuation element includes a second actuation element that is a wire within the lumen.

6. The medical device of claim 1, wherein the at least one actuation element includes a first flexible actuation element having a proximal end operatively coupled to the handle and a distal end operatively coupled to the first piston, and a second flexible actuation element having a proximal end operatively coupled to the handle and a distal end operatively coupled to the second piston.

7. The medical device of claim 1, wherein the sheath includes at least one barrier preventing a release of the first agent from the first chamber.

8. The medical device of claim 1, wherein the distal portion of the sheath is removably attached to a remainder of the sheath.

9. The medical device of claim 1, wherein the second agent is configured to be released radially outward from the first tube via the plurality of holes.

10. The medical device of claim 1, wherein the second agent includes a fluid or a powder.

11. The medical device of claim 1, wherein a diameter of each of the plurality of holes is less than 2 mm.

12. A medical device comprising:
a handle including an actuator; and
a sheath extending from the handle, wherein a distal portion of the sheath includes:
a first chamber including a first agent;
a second chamber including a second agent;
a tube disposed within the first chamber, wherein the tube has an internal lumen defining the second chamber, and wherein a wall of the tube includes a plurality of holes; and
at least one actuation element is configured to transmit a force from the actuator to each of a first piston received within the first chamber and a second piston received within the second chamber;
wherein each of the plurality of holes is configured to isolate the first agent from the second agent in the second chamber when the at least one actuation element receives no force and to release the second agent from the second chamber through the plurality of holes to mix with the first agent when the at least one actuation element receives the force.

13. The medical device of claim 12, wherein the at least one actuation element includes at least one of a wire, a tube, or a fluid.

14. The medical device of claim 12, wherein the at least one actuation element is a first actuation element, and further comprising a second actuation element, wherein the second actuation element includes at least one of a wire or a tube.

15. A medical device comprising:
a handle including an actuator;
a sheath extending from the handle, wherein the sheath includes:
a first chamber including a first agent and a second chamber including a second agent, wherein each of the first chamber and the second chamber is disposed in a distal portion of the sheath; and
a first piston received within the first chamber and a second piston received within the second chamber; and
a tube configured to transmit a force from the actuator to at least one of the first piston and the second piston,
wherein the second chamber is defined by a first tube disposed within the first chamber,
wherein a wall of the first tube includes a plurality of holes, each of the plurality of holes has a sufficiently small diameter and has a sufficient length through the wall of the tube such that the second agent does not pass through the plurality of holes until a force is exerted by the second piston,
wherein a distalmost end of the first tube is proximal of an opening in a distalmost end of the sheath, the opening of the distalmost end of the sheath being coaxial with the first and second chambers.

16. The medical device of claim 15, wherein the wall of the first tube including the plurality of holes is a radial wall.

17. The medical device of claim 12, wherein each of the plurality of holes has a sufficiently small diameter and has a sufficient length through the wall of the tube such that the second agent does not pass through the plurality of holes until a force is exerted by the second piston.

18. The medical device of claim 12, wherein the sheath includes at least one barrier preventing a release of the first agent from the first chamber; wherein the at least one barrier is positioned at a distalmost opening of the sheath.

19. The medical device of claim 12, wherein a viscosity of each of the first agent and the second agent is sufficiently high to prevent the first agent and the second agent from passing through a distal opening of the sheath without a force being applied to the first piston.

* * * * *